(12) United States Patent
Koiso et al.

(10) Patent No.: US 6,327,892 B1
(45) Date of Patent: Dec. 11, 2001

(54) APPARATUS AND METHOD FOR MEASURING OXYGEN DIFFUSING CAPACITY AND HEATING PACKET

(75) Inventors: Yoshihiko Koiso; Naoto Wagatsuma; Yoshiki Matsumoto; Masayuki Fujisawa; Koichi Yata; Kohshi Ochi, all of Hiratsuka (JP)

(73) Assignee: Japan Pionics Co., Ltd., Tokyo (JP)

( * ) Notice: Subject to any disclaimer, the term of this patent is extended or adjusted under 35 U.S.C. 154(b) by 0 days.

(21) Appl. No.: 09/214,932
(22) PCT Filed: May 15, 1998
(86) PCT No.: PCT/JP98/02159
 § 371 Date: Jan. 15, 1999
 § 102(e) Date: Jan. 15, 1999
(87) PCT Pub. No.: WO98/52015
 PCT Pub. Date: Nov. 19, 1998

(30) Foreign Application Priority Data

May 16, 1997 (JP) .................................................. 9-143493

(51) Int. Cl.[7] .................................................. G01N 15/08
(52) U.S. Cl. .................................................. 73/38
(58) Field of Search ................... 73/38; 607/108; 525/371; 426/105, 106

(56) References Cited

U.S. PATENT DOCUMENTS

| | | | |
|---|---|---|---|
| 4,852,389 | * 8/1989 | Mayer et al. | 73/38 |
| 5,021,515 | * 6/1991 | Cochran et al. | 525/371 |
| 5,904,710 | * 5/1999 | Davis et al. | 607/108 |

* cited by examiner

*Primary Examiner*—Helen Kwok
*Assistant Examiner*—Jay L. Politzer
(74) *Attorney, Agent, or Firm*—Sterne, Kessler, Goldstein & Fox P.L.L.C.

(57) ABSTRACT

The present invention provides a measuring apparatus and method for measuring the quantity of ventilation, whereby the quantity of ventilation correlates to the heating characteristics. [The present invention is also] able to measure the quantity of ventilation of a gas permeable packing material used in heating packets in a short period of time, regardless of the type or pore diameter of the packing material. The present invention provides heating packets displaying stable heating characteristics. In the present invention, one surface of a gas permeable packing material is exposed to the atmosphere, while the opposite surface is scavenged with a carrier gas which does not include oxygen. The present invention measures the oxygen diffusing capacity, [as the diffusion of oxygen] from the atmosphere through the gas permeable packing material, by measuring the concentration of oxygen in the carrier gas after scavenging. Also, the present invention provides body, pocket, and shoe heating packets wherein the quantity of ventilation is regulated by the oxygen diffusing capacity.

17 Claims, 7 Drawing Sheets

FIG.3A
FIG.3B
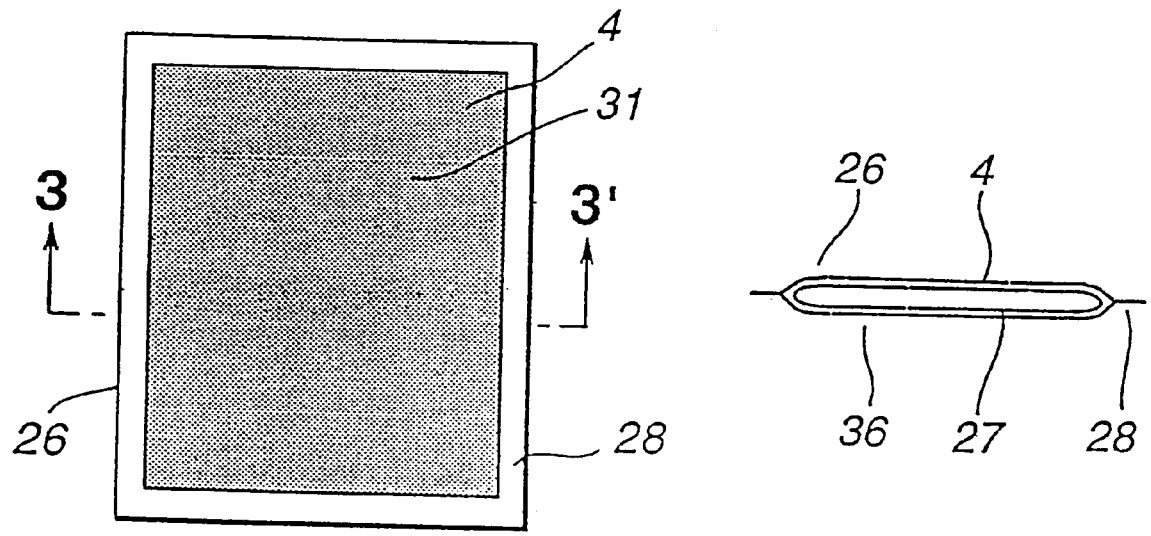
FIG.4
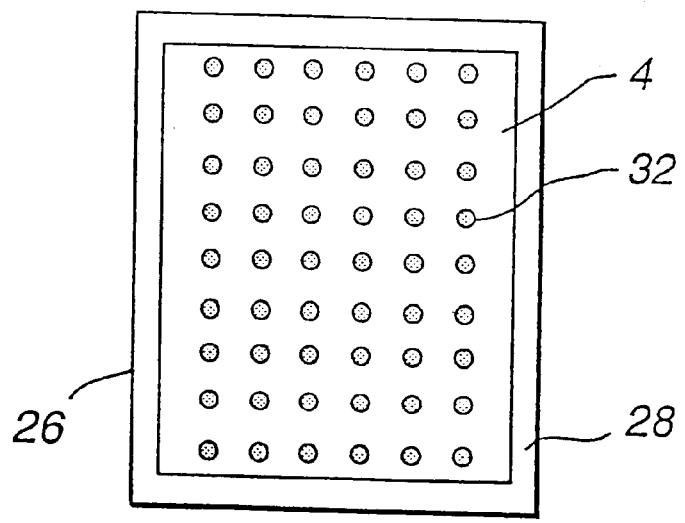

APPARATUS AND METHOD FOR MEASURING OXYGEN DIFFUSING CAPACITY AND HEATING PACKET

TECHNICAL FIELD

The present invention relates to a method and apparatus for measuring the gas permeability of the gas permeable packing material, and a heating packet using a gas permeable packing material with the quantity of ventilation regulated by oxygen diffusing capacity. The present invention relates to an apparatus for measuring oxygen diffusing capacity and a method for measuring oxygen diffusing capacity, for measuring the gas permeability of a gas permeable packing material used in pocket heaters and oxygen scavengers, and a heating packet with quantity of ventilation regulated by oxygen diffusing capacity.

BACKGROUND ART

Up to now, heating packets have been made of a heat generating composition, composed mainly of oxidative metal powders which generate heat upon contact with the oxygen in the air, which are enclosed in a gas permeable inner pouch, then sealed within an airtight outer pouch. These heating packets are used as medical devices, or as disposable pocket heaters for body warming. Furthermore, heating packets used for maintaining body temperature include the following: body heating packets used on the shoulders and lower back, pocket heating packets used in pockets and gloves, and shoe heating packets inserted in shoes.

The quantity of the heat generating composition, the proportions of the constituents of the heat generating composition, and the quantity of ventilation of the inner pouch of these heating packets are established according to usage, so that the heating packet attains the desired maximum temperature, time required to reach the desired temperature (rise time), and duration of heat production.

This heat generating composition is a mixture of oxidative metal powder, activated carbon, inorganic electrolytes, water, and so forth. Generally, iron powder is used as the oxidative metal powder. The heat generating composition generates heat when the oxidative metal powder becomes a metal oxide upon contact with the oxygen in the air.

Also, the gas permeable packing material used as the inner pouch may be one of the following: (1) a gas impermeable sheet wherein comparatively large holes, with equivalent diameters of 0.03–0.5 mm, are formed using needles or electric discharge; (2) nonwoven fabric, with limited gas permeability, formed by the superposition and thermocompression bonding of synthetic fibers of polyethylene, polypropylene, or the like; or (3) material (fine pored film) formed by dispersing a fine powder of calcium carbonate, barium sulfate, or the like in synthetic resin such as molten polyethylene, polypropylene, or the like, forming this into a film, then drawing the film to form fine pores with equivalent diameters of 10 $\mu$m or less. Furthermore, nonwoven fabric or the like may be laminated on these gas permeable packing materials.

Here, the heating characteristics of the heating packet can be controlled by methods such as the following: the method of adjusting the proportions of the constituents of the heat generating composition as noted above; the method of controlling the quantity of oxygen supplied to the heat generating composition. Furthermore, the heating characteristics can be controlled by both the adjustment of the heat generating composition and the control of the quantity of ventilation through the gas permeable packing material. However, the heating characteristics are generally set by adjusting the quantity of ventilation through the gas permeable packing material used as the Inner pouch. Known methods are employed for measuring the quantity of ventilation through these gas permeable packing materials. Proposed methods include the following: (1) methods using the Gurley permeability measuring method (JIS P 8117) (Japanese Patent Publication No. 7-90030, Japanese Patent Laid-open Publication No. 8-80317), (2) methods using the Frazier-type tester (JIS L 1018, JIS L 1096) (Japanese Patent Laid-open Publication No. 7-67907), and (3) methods using the water vapor permeability measuring method (JIS Z 0208) (Japanese Patent Laid-open Publication No. 7-124192, Japanese Patent Laid-open Publication No.8-92075). These methods are used in the design and quality control of the heating characteristics of heating packets.

Also, the official methods for measuring the heating characteristics of heating packets are the testing methods prescribed in the Japanese Industrial Standards (JIS S 4100). According to these, the heating characteristics are measured using a temperature measuring apparatus prescribed in JIS S 4100, under conditions of 20° C. external temperature and 65% relative humidity. The regulations prescribe that the heating characteristics be expressed as the time from the start of the heating operation until a temperature of 40° C. is reached (rise time), the maximum temperature reached (maximum temperature), and the time for which temperatures of 40° C. or more are maintained (continuation time).

The heating packet generates heat because of the oxidative reaction which occurs when oxygen is supplied by the oxygen in the air passing through the fine holes in the gas permeable packing material over a long period of time and the oxygen and oxidative metal powder (iron powder is a representative metal powder) come into contact.

However, the aforementioned method for measuring the quantity of ventilation depends on the size of the pores, form of the pores, type of material, and composition of the gas permeable packing material forming the inner pouch. There is no correlation between the measured value for the quantity of ventilation and the temperature characteristics. As a result, a problem is that the design and quality control for the heating packet are not adequate.

The aforementioned (1) Gurley gas permeability measurement method is constituted so that the weight of the gas chamber of the measurement apparatus operates as a pressure difference between the front and back of the gas permeable packing material. This is specifically a method for measuring the time necessary for a constant volume of gas to pass through the gas permeable packing material.

This measurement method is able to make the measurements for a packing material having relatively large pores, with equivalent diameters of 0.03–0.5 mm and formed with pins or electrical discharge, in several seconds to several minutes. However, a long period of time, such as several thousand to ten thousand seconds or more, is necessary for measuring a gas permeable packing material having a large number of small holes, such as a gas permeable packing material formed by dispersing a fine powder of calcium carbonate, barium sulfate, or the like in synthetic resin such as molten polyethylene, polypropylene, or the like, forming this into a film, then drawing the film to form fine pores with equivalent diameters of 10 $\mu$m or less. Moreover, reproducibility is poor because the measured values fall outside the range (2–1800 seconds/100 ml) of the Gurley gas permeability measurement method itself.

Furthermore, there are cases where the same heating characteristics are given even when the Gurley gas permeability measurement values differ markedly depending on the type of gas permeable packing material. The problem is that there is no correlation between the values measured for the quantity of ventilation and heating characteristics. Also, the (2) method using a Frazier-type tester is a method for measuring mainly the gas permeability of textiles. This is a method which applies a pressure difference of 12.7 mmH$_2$O between the front and back surfaces of the gas permeable packing material. This method can be applied to the measurement of a gas permeable packing material with large air holes. However, the quantity of ventilation is too small in the case of a gas permeable packing material with fine pores of 5 μm or less and this measurement method cannot measure outside of Its range (0.3–400 cc/cm$^2$/sec). Furthermore, (3) the water vapor permeability measurement method is a method for finding water vapor permeability from the amount of water vapor which diffuses through the gas permeable packing material under conditions of moisture saturation, without applying a pressure difference between the front and back surfaces of the gas permeable packing material. This appears to be a superior method. However, depending on the type of the gas permeable packing material, there is no correlation between the heating characteristics and the measured value of water vapor permeability. This applies in particular to the case of a gas permeable packing material which absorbs moisture or a gas permeable packing material having fine pores. Because of these issues, there is a strong desire for the development of a method for measuring the quantity of ventilation, which can measure the quantity of ventilation quickly and precisely, regardless of the type of gas permeable packing material, and with which a correlation with heating characteristics is attained.

Also, because of the lack of correlation between heating characteristics and quantity of ventilation of the gas permeable packing material used as the inner pouch as noted above, it has heretofore been impossible to design the heating characteristics with good precision and to have quality control for body heating packets, pocket heating packets, or shoe heating packets.

For this reason, it is desirable to develop heating packets having the desired heating characteristics and having stable heating characteristics.

In the case of shoe heating packets, the only heating packets available differ markedly from the desired heating characteristics, despite the extreme market requirements, for the aforementioned reasons. For this reason, it is desirable to develop heating packets having the desired heating characteristics and having stable heating characteristics. Therefore, it is an object of the present invention to provide a method for measuring the quantity of ventilation which correlates to heating characteristics and which can measure the quantity of ventilation quickly and precisely, regardless of the type of gas permeable packing material. It is another object of the present invention to provide an apparatus for measuring the quantity of ventilation which correlates to heating characteristics and which can measure the quantity of ventilation quickly and precisely, regardless of the type of gas permeable packing material.

Furthermore, it is another object of the present invention to provide a heating packet having the desired heating characteristics and having stable heating characteristics. It is another object of the present invention to provide various types of heating packets, as body warmers, pocket warmers, and shoe warmers.

DISCLOSURE OF THE INVENTION

As a result of their diligent research into solving these problems, the inventors discovered a correlation between the heating characteristics of the heating packet and the oxygen diffusing capacity. They accomplished this by placing a gas permeable packing material with one surface exposed to the atmosphere and scavenging the other surface with a carrier gas which does not include oxygen, and finding the oxygen diffusing capacity, which is the quantity of the oxygen gas in the atmosphere passing through the gas permeable packing material and diffusing into the carrier gas, as the standard of gas permeability. Furthermore, they discovered that they could use the gas permeability, determined with the oxygen diffusing capacity as a standard, and determine the quantity of ventilation appropriate for body warmers, pocket warmers, and shoe warmers, whereby they attained heating packets with stabilized heating characteristics and arrived at the present invention.

Specifically, the present invention is a method for measuring the oxygen diffusing capacity of a gas permeable packing material, by exposing one surface of a gas permeable packing material to the atmosphere and scavenging the other surface with a carrier gas which does not include oxygen, then measuring the gas permeability of the gas permeable packing material from the concentration of oxygen gas in the carrier gas after scavenging.

Also, the present invention is an apparatus for measuring the oxygen diffusing capacity of a gas permeable packing material which is provided a diffuser, wherein the oxygen gas in the atmosphere diffuses into the carrier gas through the gas permeable packing material, when one surface of a gas permeable packing material is exposed to the atmosphere and the other surface is scavenged with the aforementioned carrier gas.

Furthermore, the present invention is a body warming heating packet comprising a heat generating composition, which generates heat upon contact with oxygen in the air, within a gas permeable inner pouch and further sealed within a non-gas permeable outer pouch, wherein one surface of the inner pouch is a gas permeable packing material with an oxygen diffusing capacity corresponding to a range of 1100±220 Nl/m$^2$ 24h (same below) measured when one surface of a gas permeable packing material is exposed to the atmosphere and the other surface is scavenged with the aforementioned carrier gas at a flow rate of 0.193 Nl/cm$^2$ h per unit area of the gas permeable packing material, under conditions of 20° C. and 65% relative humidity.

Furthermore, the present invention is a pocket warming heating packet comprising a heat generating composition, which generates heat upon contact with oxygen in the air, within a gas permeable inner pouch and further sealed within a non-gas permeable outer pouch, wherein one surface of [the inner pouch] is a gas permeable packing material with an oxygen diffusing capacity corresponding to a range of 1600±350 Nl m$^2$24h measured when one surface of a gas permeable packing material is exposed to the atmosphere and the other surface is scavenged with the aforementioned carrier gas at a flow rate of 0.193 Nl/cm$^2$ h per unit area of the gas permeable packing material, under conditions of 20° C. and 65% relative humidity.

Additionally, the present invention is a shoe warming heating packet comprising a heat generating composition, which generates heat upon contact with oxygen in the air, within a gas permeable inner pouch and further sealed within a non-gas permeable outer pouch, wherein one surface of [the inner pouch] is a gas permeable packing material with an oxygen diffusing capacity corresponding to a range of 5500±1100 Nl/m² 24h measured when one surface of a gas permeable packing material is exposed to the atmosphere and the other surface is scavenged with the aforementioned carrier gas at a flow rate of 0.193 Nl/cm² h per unit area of the gas permeable packing material, under conditions of 20° C. and 65% relative humidity.

In the present invention, the carrier gas which does not include oxygen is preferably nitrogen, but other gases such as argon, helium, carbon dioxide, or the like may also be used without any particular restrictions. Moreover, in the present invention, the phrase "not including oxygen" does not exclude the inclusion of oxygen at a level which does not influence the measurement of gas permeability.

BRIEF DESCRIPTION OF THE DRAWINGS

FIG. 3 is an example of the inner pouch using the gas permeable packing material having small pores; (a) is a plane diagram and (b) is a cross sectional view at line 3–3';

FIG. 4 is an example of the inner pouch using the gas permeable packing material having small pores in part;

BEST MODE FOR CARRYING OUT THE INVENTION

The present invention is applied to the measurement of the quantity of ventilation through a gas permeable packing material used in heating packets and oxygen scavengers. Also, the present invention is applied to body warmers, pocket warmers, and shoe warmers wherein the quantity of ventilation is regulated by the oxygen diffusing capacity.

The method and apparatus for measuring oxygen diffusing capacity relating to the present invention can be used for measuring the quantity of ventilation for highly gas permeable packing materials, as well as packing materials with very low gas permeability, in a short period of time. With the method and apparatus for measuring oxygen diffusing capacity relating to the present invention, the front and back surfaces of the gas permeable packing material are maintained under equal total pressure conditions and oxygen diffuses therethrough because of the difference in partial pressure of the oxygen in the gases contacting these surfaces. This quantity of oxygen is measured with the present invention. The method and apparatus relating to the present invention are constituted so that measurement is made under conditions where the difference in total pressure between the two surfaces becomes nearly zero.

The surface of the gas permeable packing material which is in contact with the air is kept in continuous contact with fresh air, specifically in a state where the surface in contact with air is exposed to the atmosphere. Meanwhile, it is required that fresh nitrogen be continually supplied to the surface of the gas permeable packing material which is in contact with nitrogen, so that the difference in oxygen partial pressure remains constant even in the case where oxygen diffuses therethrough. Specifically, methods for the continual supply and exhaust of nitrogen are used.

The present invention is explained more specifically using the drawings.

Figure 1:
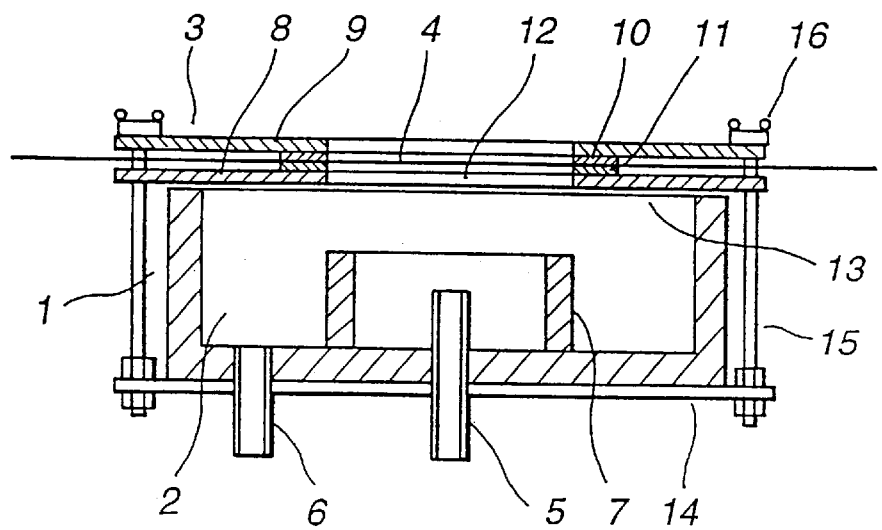
FIG. 1 shows an example of a cross sectional view of a diffuser.
Figure 2:
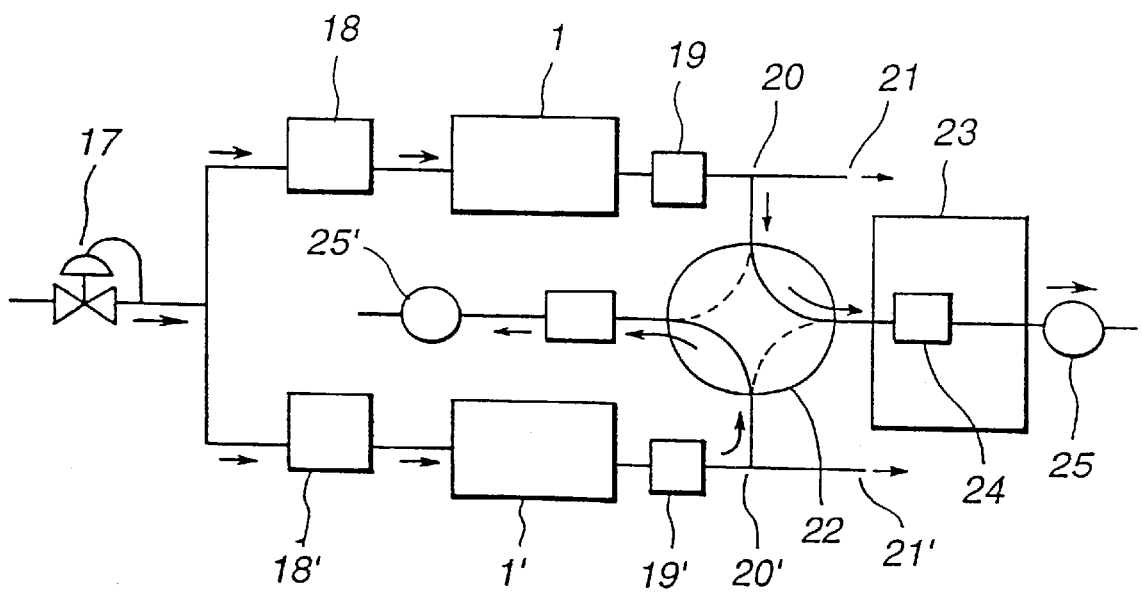
FIG. 2 is a block diagram showing the principle of the apparatus for measuring oxygen diffusing capacity relating to the present invention.
Figure 5:
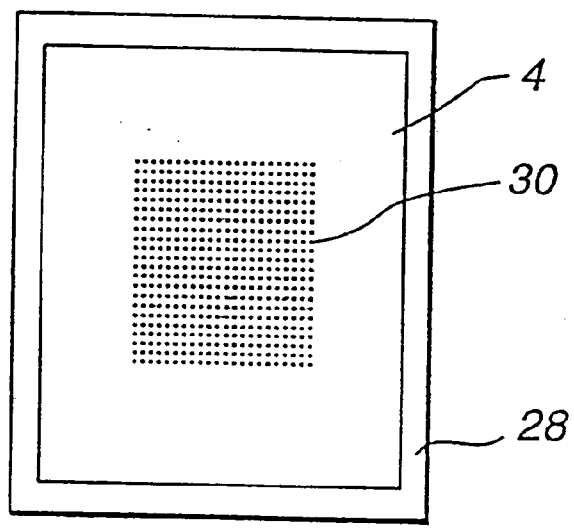
FIG. 5 is an example of an inner pouch using the gas permeable packing material wherein pin holes are concentrated in the center.

FIG. 1 shows an example of a cross sectional view of the diffuser of the apparatus for measuring oxygen diffusing capacity relating to the present invention. FIG. 2 shows an example of the apparatus for measuring oxygen diffusing capacity wherein two diffusers are established in a parallel configuration.

In FIG. 1, the diffuser 1 comprises a chamber 2 and a cover portion 3. The chamber 2 is cylindrical and a nitrogen gas supply tube 5 is established in the central portion thereof. An exhaust tube 6 is established in an area near the outer perimeter of the chamber. Within the chamber, a cylindrical partition barrier 7 is established in order to prevent the nitrogen gas from being directly exhausted (short pass). The cover portion 3 comprises metal frames 8, 9 and backing sheets 10, 11. An airtight seal with the chamber is maintained by means of a ring-shaped sheet backing 13. A hollow portion equivalent to the measured surface 12 of the gas permeable packing material 4 is formed in both the frames 8, 9 and backing sheets 10, 11.

The gas permeable packing material 4 is held between the backing sheets 10, 11; the entirety is affixed between the base frame 14 and cover portion 3, which are screwed together with the bolt 15 and nut 16.

With the apparatus in this state, nitrogen gas flows at a constant flow rate from the nitrogen gas supply tube 5. The oxygen diffusing capacity of the gas permeable packing material can be measured by measuring the concentration of oxygen in the gas flowing out from the exhaust tube 6. FIG. 2 shows the constitution of the apparatus for measuring oxygen diffusing capacity having a series of two diffusers. The nitrogen gas is supplied to the diffuser 1 from a pressure reducing valve 17 via the nitrogen gas flow controller 18. The exhaust gas of the diffuser 1 is exhausted via the oxygen concentration detector 19 and then the purge line 21. FIG. 2 also shows the case of measuring oxygen concentration using one gas chromatograph 23. The gas flow path from the diffuser 1 is connected to the gas chromatograph 23 via a branched portion 20 and switching valve 22. A gas aspirator 25 is connected to the rear of the gas sampling portion 24 of the gas chromatograph 23. The apparatus is thereby set to attain a constant flow rate even in the event of flow path resistance from the branched portion 20 to the gas sampling portion 24.

In addition to the structure and form of diffuser shown in FIG. 1, the present invention can also have a diffuser wherein the chamber is a square box or elliptical cylinder. Also, in FIG. 1, the scavenging gas, which is nitrogen gas, flows from the central area of the chamber toward the periphery. It is also possible for the scavenging gas to flow from the periphery to the center, or in the case of a box-shaped chamber, to flow from one end to the opposite end, parallel to the measured surface. Chamber size corresponds to the size of the measured surface of the gas permeable packing material to be measured. Chamber size is not limited so long as the nitrogen gas uniformly scavenges the measured surface of the gas permeable packing material, and the gas In the chamber is replaced in a short period of time.

There are no restrictions on the type and shape of frame, which can be square, rectangular, or round. The size and form of the frame are not restricted if a measured surface, of sufficient area to represent the gas permeability of the gas permeable packing material, is attained. If the area of the measured surface is too small, the precision of the measurement is reduced and if too large, it becomes difficult to maintain the flatness of the measured surface. As a result, the area is usually 2–300 $cm^2$, and preferably 10–100 $cm^2$.

The backing sheet may comprise a backing of synthetic resin or rubber backing, having the elasticity of rubber, so as to prevent gas leakage even in the case of the gas permeable packing material having a slightly irregular surface. FIG. 1 shows an example of a structure wherein the chamber and cover portion can be separated, but it is also possible for the chamber portion and cover portion to be formed as a unit. Also, it is possible to screw the gas permeable packing material to the chamber in a single operation using a pneumatic cylinder, lever, or rotating handle.

Moreover, in the case where the gas permeable packing material is mounted on the chamber, it is preferably mounted in accord with the state of use in a heating packet. Specifically, the packing material is preferably mounted on the chamber in such a manner that the surface which corresponds to the outside of the inner pouch is exposed to the atmosphere, and the surface which corresponds to the inner surface of the inner pouch becomes the surface scavenged with nitrogen.

A gas chromatograph or an oxygen densitometer using an oxygen gas sensor can be used for measuring the oxygen concentration. In the case of using either instrument, it is necessary to use a flow path structure with little fluid resistance, in order that no pressure difference occur between the atmosphere and the interior of the diffuser chamber. For this reason, a method established close to the exhaust tube portion within the chamber, or a method established directly beyond the exhaust tube portion, is used when taking measurements using an oxygen gas sensor. In the case of taking measurements with a gas chromatograph, it is preferable maintain conditions so that no pressure difference occurs between the chamber and atmosphere, for example, by using a method of aspirating gas at a constant flow rate to the sampling portion of the gas chromatograph.

Furthermore, measurement efficiency can be improved as follows. The disposition of two parallel diffusers, as shown in FIG. 2, makes it possible to take measurements with one series, while replacing the sample in the other.

Otherwise, the measured surface can be made relatively large and the measured value can be calculated as a representative value for the gas permeable packing material, depending on the distribution of the air holes in the gas permeable packing material, for example, when the air holes are continuous like a dotted line or the holes are concentrated in the central portion.

The nitrogen gas supplied to the diffuser is preferably highly purified nitrogen gas, to permit high precision measurement of a gas permeable packing material with little oxygen diffusing capacity. Also, if the amount of nitrogen gas supplied is too large, this can cause deformation or oscillation of the sample surface. If too small, the concentration of the oxygen in the nitrogen gas becomes high because of oxygen diffusion and the difference in oxygen partial pressure between the front and back of the gas permeable packing material becomes undesirably small. As a result, nitrogen gas is usually supplied at 50–2000 $ml/cm^2$ h, and preferably 100–500 $ml/cm^2$ h, per unit area of the measured surface of the gas permeable packing material.

The flow rate of nitrogen supplied can be controlled using a flow meter and needle valve. Otherwise, a mass flow controller can control the flow rate with good precision and is therefore convenient.

In the diffuser, a difference between the pressure on the side exposed to the atmosphere and the pressure within the chamber may result in a flow of oxygen which is not a result of diffusion from the atmosphere side into the chamber, or a flow of nitrogen from the chamber to the atmosphere side. This is as a result of a viscous flow occurring on the basis of the pressure difference for a gas permeable packing material with large pore diameters. Consequently, while this may vary depending on pore diameter, the apparatus is usually constituted so that the pressure difference between the two sides is 3 $mmH_2O$ or less, and preferably 1 $mmH_2O$ or less, by increasing the diameter of the chamber exhaust tube or employing the method of aspiration from the exhaust tube. Oxygen concentration can be measured using a gas chromatograph with a thermal conductivity detector; it can also be simple to use a zirconia electrode oximeter. Moreover, in the case of measuring oxygen concentration with a gas chromatograph using the constitution in FIG. 2, the length of the purge line 21 and aspiration rate of the sampling gas are considered in order that there be no mixing with or aspiration of outside air from the purge line 21. In any event, it is necessary to operate the apparatus so that no large pressure difference occurs between the outside air pressure and the pressure within the diffuser chamber. The gas permeable packing material which is the subject of measurement in the present invention includes packing materials having pores through which gas diffuses, regardless of the quantity of ventilation. Usually, the pores have equivalent diameters of 1 mm or less. This term includes any packing material which is the subject of measurement in the present invention, even this is a material which is generally called a film, sheet, or membrane, so long as it has pores with equivalent diameters of 1 mm or less and is gas permeable. Consequently, no restrictions are applied to the form of the pores, the thickness, or type of gas permeable packing material.

Moreover, "equivalent diameters" means-the area of a hole, expressed as the diameter of a round hole, for the pores which may be elliptical, square, slit, or triangular. Gas permeable packing materials having pores with equivalent diameters of 1 mm or more may also be the subject of measurement in the present invention. In that case, however, the measured value of oxygen diffusing capacity may be incorrect due to the expansion of hole diameters due to a flow of oxygen which is not a result of diffusion from the atmosphere side into the chamber, or a flow of nitrogen from the chamber to the atmosphere side.

The method and apparatus for measuring oxygen diffusing capacity relating to the present invention can measure the quantity of ventilation, with good precision and regardless of the form and size of the pores, as the oxygen diffusing capacity. Specifically, the present invention can measure with good precision materials having relative large holes with equivalent diameters of 0.03–0.5 mm, such as the following: gas permeable packing material comprising a non-gas permeable film having holes formed mechanically using pin-like protrusions, as means for providing gas permeability to the gas permeable packing material; gas permeable packing material with pores punched in a mold; or a gas permeable packing material wherein holes are formed when part of a film or membrane is melted with the application of electrical discharge or a heated item with pin-like protrusions. Also, the present invention can measure with good precision and in a short period of time a gas permeable packing material which is made as follows: calcium carbonate or barium sulfate is blended in synthetic polyolefine resin such as polyethylene or polypropylene; this is extruded to form a film; then a large number of pores with equivalent diameters of 10 $\mu$m or less are formed by uniaxial drawing or biaxial drawing. Otherwise, the present invention can also measure with good precision and in a short period of time a gas permeable packing material, wherein the gas permeability of nonwoven fabric, comprising heat-fusible synthetic fibers such as polyethylene or polypropylene, is limited by thermocompression bonding.

The gas permeability of these gas permeable packing materials, without further processing or when applied to nonwoven fabric and formed into a gas permeable packing material for a heating packet, can be measured with the present invention. The apparatus and method for measuring the oxygen diffusing capacity relating to the present invention can measure, as oxygen diffusing capacity, the gas permeability of gas permeable wallpaper, gas permeable packing material for oxygen scavengers, or apparel which is gas permeable but impermeable to water, as well as the gas permeable packing material for heating packets. Furthermore, the present invention can also measure the quantity of ventilation of materials having a fine fibrile structure and comprising drawn film or tubes of polyfluoroethylene resin.

In the case of measuring the quantify of ventilation for gas permeable packing materials for heating packets in particular, the present invention is a very useful measurement method because measurements are made under conditions similar to those conditions under which the heating packet is actually used. Specifically, when oxygen diffusing capacity is measured, one surface of the gas permeable packing material is exposed to the atmosphere. This corresponds to the state wherein the heating packet is in contact with outside air. The other surface is scavenged with nitrogen; this corresponds to the state wherein the concentration of oxygen within the heating packet is nearly zero.

Consequently, the present invention has applications, as a method for measuring gas permeability for heating packets, which are not apparent in conventional methods for measuring gas permeability.

Generally, a heating packet is filled with a heat generating composition within a flat, gas permeable inner pouch. While this varies depending on the type and purpose of heating packet, it is often the case that one surface of the inner pouch is a gas permeable packing material, while the other surface is non-gas permeable packing material.

FIGS. 3–6 show examples of the inner pouches of commercially available heating packets made with these gas permeable packing materials. FIG. 3($b$) shows a cross sectional view taken at line 3–3' in FIG. 3($a$). These inner pouches are generally made with one surface being gas permeable packing material and the other surface being non-gas permeable packing material; the edges are heat sealed together to form the flat inner pouch.

The oxygen diffusing capacity of the gas permeable packing material can be found using the equation 1 with the present invention.

In other words, it is assumed that the quantity of oxygen diffusing through the gas permeable packing material into the chamber from the atmosphere is equal to the quantity of nitrogen in the chamber diffusing through the gas permeable packing material into the atmosphere. The oxygen diffusing capacity of the gas permeable packing material is then found using the equation 1 from the quantity of nitrogen supplied and the oxygen concentration in the nitrogen after scavenging.

Oxygen diffusing capacity (Nl/m$^2$ 24h)=oxygen concentration ((%)/100)×quantity of nitrogen supplied (Nl/h)×24×1/measured area (m$^2$) [Equation 1]

Moreover, when the pore portion of the measured material is distributed in one portion of the measured surface, appropriate correction of the surface area makes it possible to find the oxygen diffusing capacity as the mean oxygen diffusing capacity of the gas permeable packing material. Also, because gas permeability is measured using the quantity of nitrogen supplied to the diffuser and the oxygen concentration in the nitrogen after scavenging, the apparatus and method for measuring oxygen diffusing capacity relating to the present invention can measure quantity of ventilation with good precision and in a short period of time, regardless of the degree of gas permeability.

When heating packets are designed using gas permeable packing materials with oxygen diffusing capacity measured in this manner, there is a strong correlation between the quantity of ventilation and the heating characteristics of the heating packet. For this reason, it is very easy to design a heating packet having the desired heating characteristics; moreover, heating packets having stable heating characteristics can be manufactured.

For example, in the case of producing heating packets wherein the oxygen diffusing capacity of the gas permeable packing material is changed, the square (R$^2$: contribution ratio) of the correlation coefficient, between the oxygen diffusing capacity and the rise time, maximum temperature, and continuation time measured with a heating test according to JIS S4100, at the point where each approaches linearity becomes 0.85 or more, preferably 0.90 or more, and more preferably 0.95 or more.

Moreover, the method for measuring oxygen diffusing capacity relating to the present invention can use another carrier gas (scavenger gas) which does not include oxygen, instead of nitrogen, for scavenging one surface of the gas permeable packing material. For example, argon, helium, or carbon dioxide can be used.

When these gases are substituted for nitrogen gas, the partial pressure difference of these gases with the atmosphere side becomes markedly larger than when nitrogen is used. Moreover, depending on the type of gas, a large quantity of that gas may migrate through to the atmosphere because the diffusion constant of the gas itself may be high. For this reason, the quantity of exhaust gas from the measuring chamber may sometimes be less than the quantity of gas supplied. Consequently, the equation 1 cannot be applied without further processing in such cases.

For example, when using helium instead of nitrogen, one must find the correct quantity of exhaust gas and substitute this for the quantity of nitrogen supplied in equation 1. Because the correct quantity of exhaust gas must be found while the partial pressure difference with the atmosphere side is maintained at 1 mmH$_2$O or less, the structure of the apparatus for measuring oxygen diffusing capacity may become somewhat more complex than when using nitrogen.

A heating packet is designed with the preferred size and heating characteristics, according to the purpose, area of use, and conditions of use.

For example, body heating packets, to be applied on the skin of the lower back or shoulders to maintain body temperature, include so-called "regular" heating packets with a relatively large surface area or "mini" heating packets with a small area. These body heating packets with different sizes have variations in their preferred heating capacities; basically, these are designed as heating packets with relatively low heating values per unit time.

Also, pocket heating packets used in pockets or gloves are designed to have a relatively high heating values per unit time, because these are used under conditions where temperature retention is poor.

Meanwhile, shoe heating packets have very high heating values per unit time, because these are used under conditions where much heat is lost because of contact with water and snow, and because of shoes' poor heat retention.

The gas permeable packing material for body heating packets relating to the present invention is a gas permeable packing material wherein the oxygen diffusing capacity is usually 1100±220 Nl/m$^2$ 24h, preferably 1100±150 Nl/m$_2$ 24h, and more preferably 1100±100 Nl/m$^2$ 24h, when measured as follows. Under conditions of 20° C. and 65% relative humidity, one surface of the gas permeable packing material is exposed to the atmosphere and the other surface is exposed to a flow of nitrogen gas at a flow rate of 0.193 Nl/cm$^2$ h, in order to scavenge the surface of the gas permeable packing material. Meanwhile, the partial pressure difference between the atmosphere side and the nitrogen gas side is 1 mmH$_2$O or less. With a conventional method for measuring the quantity of ventilation, the fluctuation of the heating characteristics is too great, the desired heating capacity cannot be attained, and quality control for the heating packets is impossible. With the method for measuring oxygen diffusing capacity relating to the present invention, however, heating packets having the desired heating characteristics are attained, at a higher precision than was possible with the prior art, by the regulation of the quantity of ventilation as noted above. Moreover, when the gas permeable packing material is used for the entire surface of one side of the inner pouch, this quantity of ventilation can be one half the aforementioned numerical value in the case where the gas permeable packing material is used for both sides of the inner pouch and both sides have equal gas permeability. Also, when used partially, one can use packing material with the quantity of ventilation calibrated according to the percentage of the area.

As noted above, the size of the inner pouch for the "regular type" of body heating packet is (90 to 110 mm)× (125 to 145 mm); the size of the inner pouch for the "mini type" is (55 to 75 mm)×(85 to 105 mm). Furthermore, some of these heating packets are 1.5 times, twice, or three times the size of the regular type. In the present invention, these are all included as body heating packets.

For pocket heating packets relating to the present invention, the quantity of ventilation for the gas permeable packing material corresponds to an oxygen diffusing capacity of usually 1600±350 Nl/m$^2$ 24h, preferably, 1600±220 Nl/m$^2$ 24h, and more preferably 1600±150 Nl/m$^2$ 24h, when measured as follows. Under conditions of 20° C. and 65% relative humidity, one surface of the gas permeable packing material is exposed to the atmosphere and the other surface is exposed to a flow of nitrogen gas at a flow rate of 0.193 Nl/cm$^2$ h, in order to scavenge the surface of the gas permeable packing material. Meanwhile, the partial pressure difference between the atmosphere side and the nitrogen gas side is 1 mmH$_2$O or less.

If the oxygen diffusing capability of the packing materials is within this range, a heating packet using such packing materials displays very good heating characteristics. In this instance as well, the quantity of ventilation, in the case when the gas permeable packing material is used for all of one side of the inner pouch, can be established with the same methods as for body heating packets, when maintaining equivalent gas permeability where the gas permeable packing material is used for all or part of the inner pouch. For the pocket heating packet relating to the present invention, the size of the inner pouch is usually (55 to 75 mm)×(85 to 105 mm). However, size is not particularly restricted, so long as the heating packet can be used in pockets or gloves.

For shoe heating packets relating to the present invention, the quantity of ventilation for the gas permeable packing material corresponds to an oxygen diffusing capacity of usually 5500±1100 Nl/m$^2$ 24h, preferably 5500±800 Nl/m$^2$ 24h, and more preferably 5500±500 Nl/m$^2$ 24h, when measured as follows. Under conditions of 20° C. and 65% relative humidity, one surface of the gas permeable packing material is exposed to the atmosphere and the other surface is exposed to a flow of nitrogen gas at a flow rate of 0.193 Nl/cm$^2$ h, in order to scavenge the surface of the gas permeable packing material. Meanwhile, the partial pressure difference between the atmosphere side and the nitrogen gas side is 1 mmH$_2$O or less. Regulating quantity of ventilation in this manner makes it possible to attain shoe heating packets, having the desired heating characteristics which were difficult to design before now. It is thereby possible to attain a comfortable warm feeling, even when these are inserted in shoes, which generally lose much heat and have poor gas permeability. Also, the inner pouches of shoe heating packets relating to the present invention may be in the form of rectangles and trapezoids, as well as a so-called "horse's hoof" shape which fits in the toe of a shoe.

The preferred embodiments of the present invention are explained in further detail on the basis of the following examples; however, the present invention is not limited by these.

Examples 1–9

Examples 1–9 are examples relating to the apparatus and method for measuring oxygen diffusing capacity relating to the present invention. Herein, examples 3–7 are examples of pocket heating packets relating to the present invention. An apparatus for measuring oxygen diffusing capacity, identical to that shown in FIGS. 1 and 2, was constructed. The instruments were constituted as follows and based on FIGS. 1 and 2.

The chamber 2 of the diffuser 1 is a stainless steel cylinder with an inner diameter of 102 mm and a depth of 37.5 mm; this contains a cylindrical partition barrier 7, 25 mm high and with an outer diameter of 60 mm, for preventing the sideways movement of the nitrogen gas. The interior volume of the chamber 2 is 285 ml.

In the central portion of the chamber 2, a nitrogen gas supply tube 5, with outer diameter 6.35 m and inner diameter 4.57 mm, is established so that it extends 15 mm from the bottom surface. Furthermore, an exhaust tube 6 is established near the edge inside the chamber.

The frame 8 has a measured surface 12 which is 72 mm×72 mm.

The nitrogen gas flow controller is a mass flow controller (ESTEC Co., SEK-400MK3).

The oxygen concentration detector 19 is a zirconia electrode oximeter (Toray Engineering, LC-750L) and is constituted to be combined with a gas chromatograph 23.

Also, the aspiration pump 25 is an aspiration pump which does not cause pulsations.

The gas permeable packing material 4 comprises a non-gas permeable packing material, of a 50 micron thick polyethylene film laminated to a nylon nonwoven fabric (Asahi Chemical Industry, N5051), wherein slit holes are formed in 31 rows at 4 mm intervals within a 32 mm width using a hole-making apparatus using a rotating blade having pin-like protrusions. Also, nine types of gas permeable packing materials with varying quantities of ventilation are produced by varying the pin hole depth in stages and changing the sizes of the pores. The pores have sizes such that the equivalent diameters are in the range of 0.03 to 0.7 mm.

The oxygen diffusing capacities of these nine types of gas permeable packing material were measured using the aforementioned apparatus for measuring oxygen diffusing capacity. Measurements were made under the following conditions: temperature of 20° C. and 65% relative humidity, a 10 Nl/h (the nitrogen supply is 0.193 Ns/cm$^2$ h per unit measured area of the gas permeable packing material) supply of nitrogen gas, and sample gas aspiration by the aspiration pump at 1.2 Nl/h. The partial pressure difference between the atmosphere and the chamber was 1 mmH$_2$O or less. In addition, the time necessary for the oxygen concentration in the chamber to reach equilibrium was 12 minutes.

Table 1 shows the results.

Figures 6A, 6B:
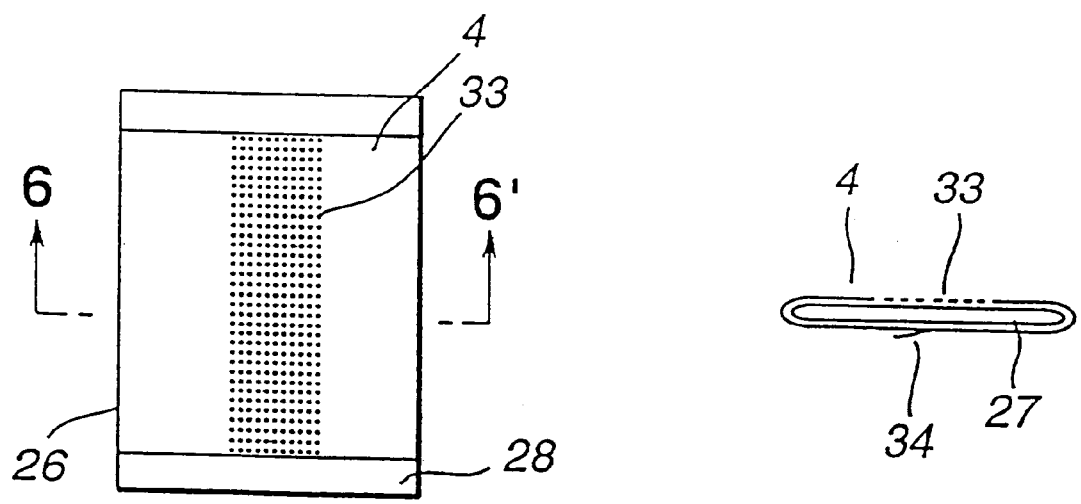
FIG. 6 is an example of an inner pouch with a back seal and using the gas permeable packing material having pin holes in the center; (a) is a plane diagram and (b) is a cross sectional view at line 6–6'.

Next, using the nine types of gas permeable packing material, 97 mm×70 mm pouches were produced by back sealing so that the pores were distributed on one side. These pouches were filled with 20 g of a heat generating composition comprising a mixture of 55 wt % of iron powder, 6 wt % of activated carbon, 12 wt % of sawdust, 3 wt % of table salt, and 24 wt % of water. These were then heat sealed to form nine flat inner pouches as shown in FIG. 6.

These inner pouches were sealed within non-gas permeable other pouches and made into heating packets.

These nine heating packets were let stand 12 hours in an environment with temperature 20° C. and 65% relative humidity and acclimated to this environment. The inner pouches were then removed and the heating characteristics were measured with the test method stipulated in JIS S 4100.

Figure 7:
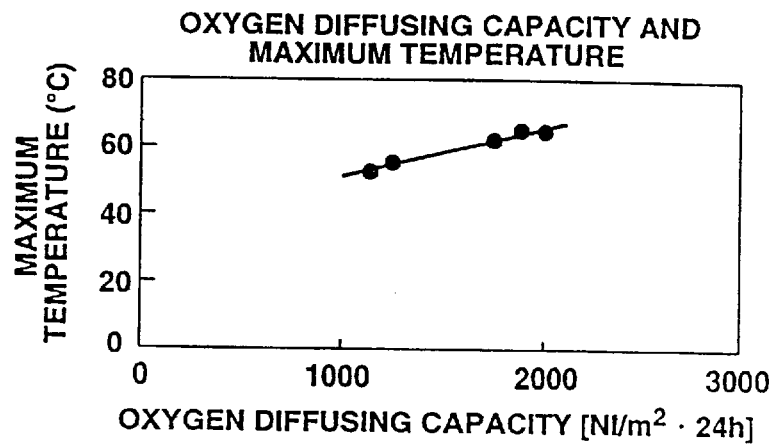
FIG. 7 is a diagram showing the properties of the relationship between the maximum temperature and the oxygen diffusing capacity in embodiments 1–9.
Figure 8:
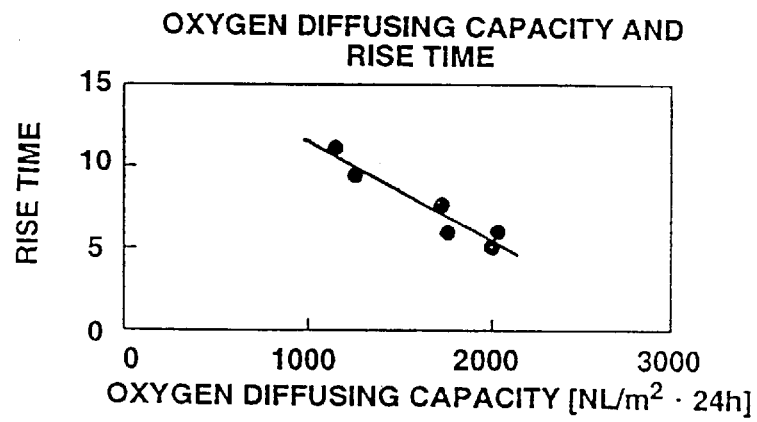
FIG. 8 is a diagram showing the properties of the relationship between the rise time and the oxygen diffusing capacity in embodiments 1–9.
Figure 9:
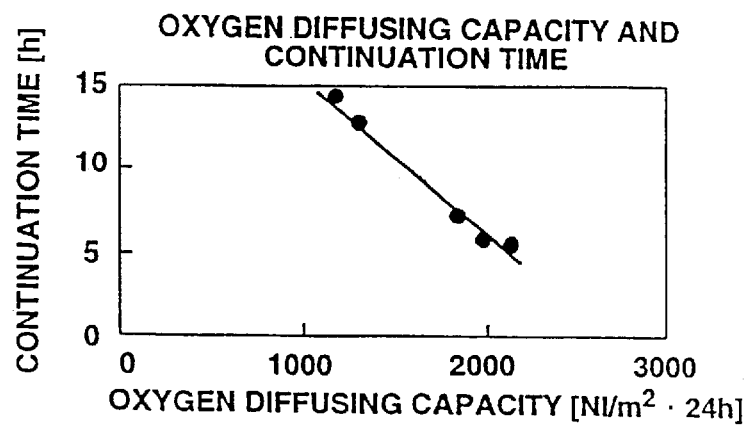
FIG. 9 is a diagram showing the properties of the relationship between the continuation time and the oxygen diffusing capacity in embodiments 1–9.

The results are shown in Table 1. FIG. 7 shows the relationship between oxygen diffusing capacity and maximum temperature (the maximum temperature reached by the heating packet). FIG. 8 shows the relationship between oxygen diffusing capacity and rise time (time necessary for the heating packet to reach 40° C. from the start of heat generation). FIG. 9 shows the relationship between oxygen diffusing capacity and continuation time (time from when the heating packet reached 40° C., then reached the maximum temperature, and returned to 40° C.). The squares ($R^2$: contribution ratio) of the correlation coefficient, between the oxygen diffusing capacity and the rise time, maximum temperature, and continuation time, at the point where each approaches linearity, were 0.915 for the maximum temperature, 0.922 for the rise time, and 0.975 for the continuation time. In this way, strong correlations of these with oxygen diffusing capacity were confirmed.

TABLE 1

| Example | Oxygen diffusing capacity (Nl/m$^2$ 24 h) | Maximum temperature (° C.) | Rise time (min) | Continuation time (h) |
| --- | --- | --- | --- | --- |
| 1 | 1125 | 52.5 | 11.5 | 14.3 |
| 2 | 1247 | 55.8 | 9.8 | 12.6 |
| 3 | 1710 | 62.2 | 7.9 | 8.0 |
| 4 | 1754 | 63.5 | 6.3 | 7.5 |
| 5 | 1766 | 61.3 | 7.5 | 7.6 |
| 6 | 1863 | 65.1 | 6.2 | 6.8 |
| 7 | 1882 | 65.6 | 6.1 | 6.4 |
| 8 | 1987 | 65.8 | 5.5 | 5.9 |
| 9 | 2032 | 63.7 | 6.3 | 6.3 |

Examples 10–13

Examples 10 to 13 are examples relating to the method for measuring oxygen diffusing capacity and apparatus for measuring oxygen diffusing capacity relating to the present invention. Among these examples, examples 11 and 12 concern body heating packets relating to the present invention. The gas permeable packing material used was four types of gas permeable packing material (Nitto Denko, BREATHRON), having different quantities of ventilation and made of porous polyethylene film having a large number of fine pores with equivalent diameters of 10 μm or less laminated to a non-woven nylon cloth. These were measured with the same method as in examples 1–9. Next, four types of pouches, 135 mm×100 mm, were prepared as follows. These gas permeable packing materials were each used as one surface; a non-gas permeable packing material, of polyethylene, nylon nonwoven fabric, polyethylene, adhesive, and releasing paper laminated together in that order, was used as the other surface. These packing materials were placed on each other so that the polyethylene surfaces were in contact and heat sealed on three sides. These four inner pouches were filled with 40 g of a heat generating composition comprising 53 wt % iron powder, 8 wt % activated carbon, 7 wt % sawdust, 4 wt % table salt, and 28 wt % water; inner pouches as shown in FIG. 3 were attained. These were then sealed within non-gas permeable outer pouches to form heating packets.

These pouches underwent the same test of temperature characteristics as did examples 1–9.

Figure 10:
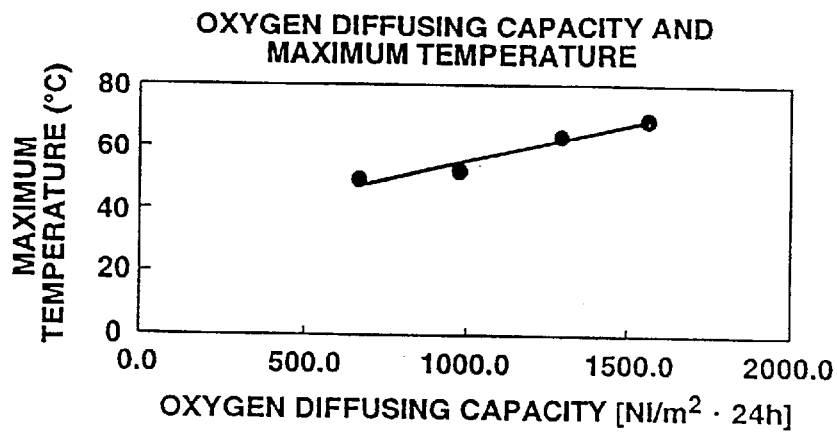
FIG. 10 is a diagram showing the properties of the relationship between the maximum temperature and the oxygen diffusing capacity in embodiments 10–13.
Figure 11:
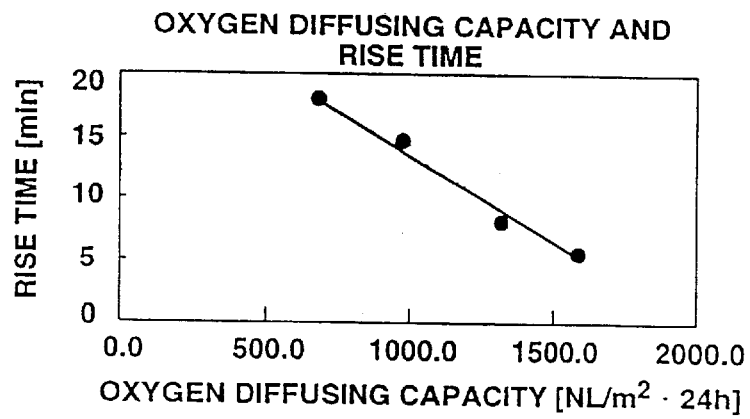
FIG. 11 is a diagram showing the properties of the relationship between the rise time and the oxygen diffusing capacity in embodiments 10–13.
Figure 12:
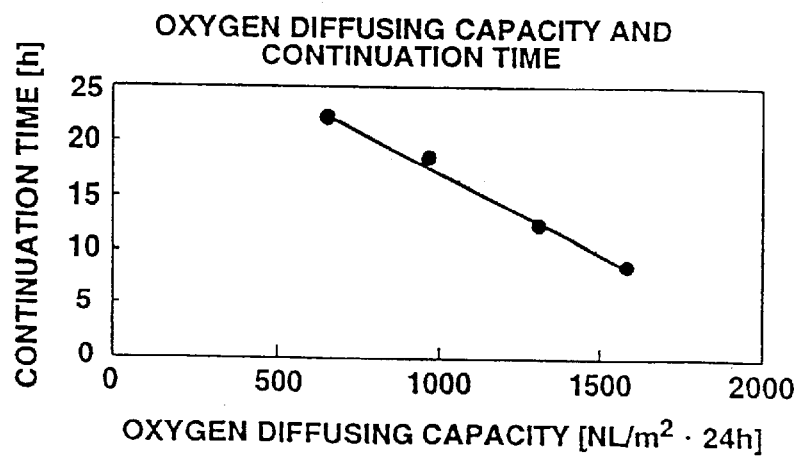
FIG. 12 is a diagram showing the properties of the relationship between the continuation time and the oxygen diffusing capacity in embodiments 10–13.

Table 2 shows the results for examples 10–13. FIG. 10 shows the relationship between oxygen diffusing capacity and maximum temperature. FIG. 11 shows the relationship between oxygen diffusing capacity and rise time. FIG. 12 shows the relationship between oxygen diffusing capacity and continuation time. The squares ($R^2$: contribution ratio) of the correlation coefficient, between the oxygen diffusing capacity and the rise time, maximum temperature, and continuation time, at the point where each approaches linarity, were 0.940 for the maximum temperature, 0.974 for the rise time, and 0.985 for the continuation time. In this way, strong correlations of these with oxygen diffusing capacity were confirmed.

TABLE 2

| Example | Oxygen diffusing capacity (Nl/m² 24 h) | Maximum temperature (° C.) | Rise time (min) | Continuation time (h) |
| --- | --- | --- | --- | --- |
| 10 | 1567 | 68.6 | 6.4 | 8.7 |
| 11 | 1310 | 62.1 | 8.5 | 12.3 |
| 12 | 988 | 51.6 | 15.0 | 18.8 |
| 13 | 677 | 49.7 | 18.0 | 22.0 |

Examples 14–21

Examples 14 to 21 are examples relating to the method for measuring oxygen diffusing capacity and apparatus for measuring oxygen diffusing capacity relating to the present invention. These examples 14 and 21 concern body heating packets relating to the present invention.

The gas permeable packing material used was eight types of gas permeable packing material (Nitto Denko, BREATHRON), having different quantities of ventilation and made of porous polyethylene film having a large number of fine pores with equivalent diameters of 10 μm, or less laminated to a non-woven woven nylon cloth. These were measured with the same method as in examples 1–9. Next, eight types of pouches, 135 mm×100 mm, were prepared as follows. These gas permeable packing materials were each used as one surface; a non-gas permeable packing material, of polyethylene, nylon nonwoven fabric, polyethylene, adhesive, and releasing paper laminated together in that order, was used as the other surface. These packing materials were placed on each other so that the polyethylene surfaces were in contact and heat sealed on three sides.

These eight inner pouches were filled with 34 g of a heat generating composition comprising 53 wt % iron powder, 8 wt % activated carbon, 7 wt % sawdust, 4 wt % table salt, and 28 wt % water; inner pouches as shown in FIG. 3 were prepared. These were then sealed within non-gas permeable outer pouches to form heating packets.

The heating characteristics of these heating packets were examined in the same way as were examples 1–9.

Figure 13:
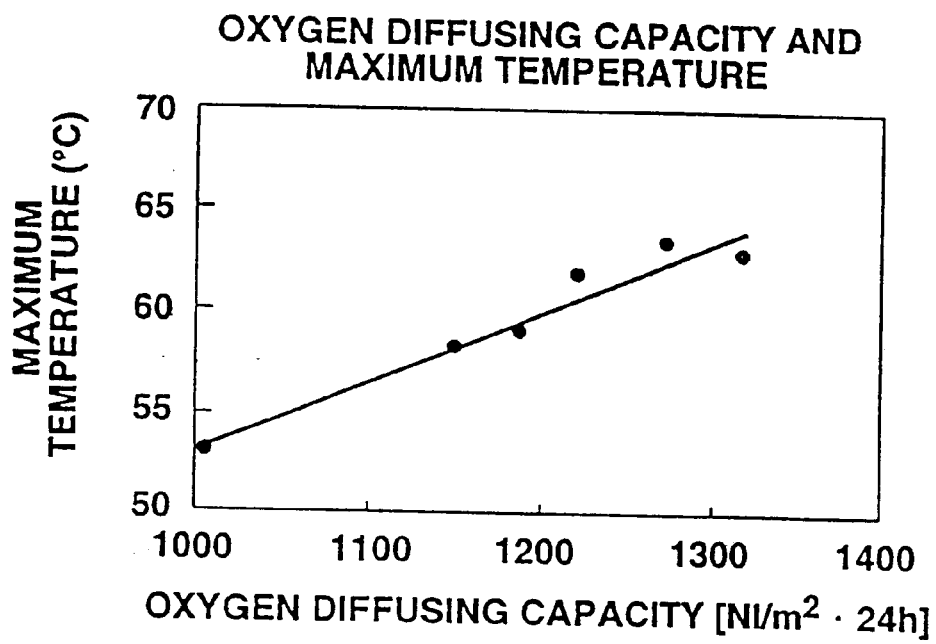
FIG. 13 is a diagram showing the properties of the relationship between the maximum temperature and the oxygen diffusing capacity in embodiments 14–21.
Figure 14:
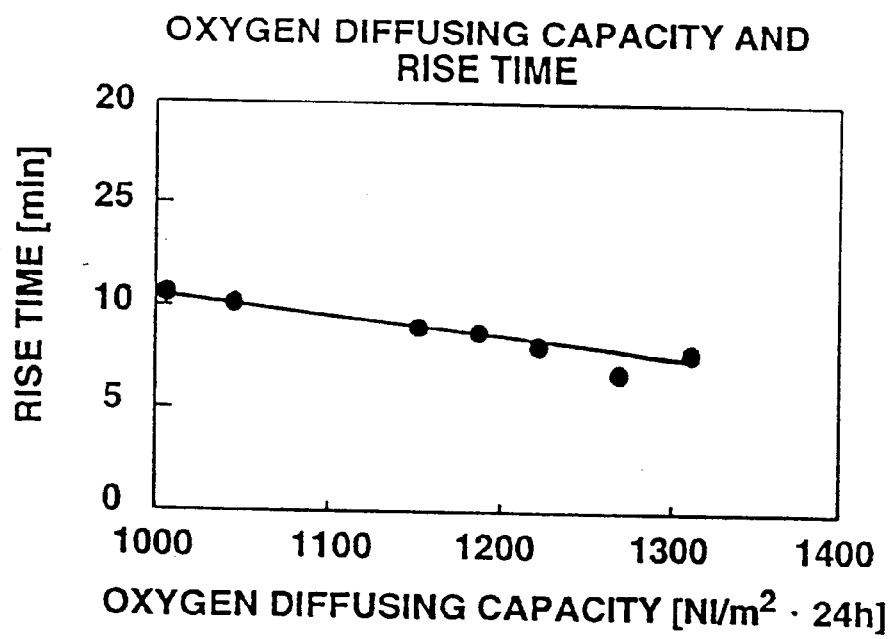
FIG. 14 is a diagram showing the properties of the relationship between the rise time and the oxygen diffusing capacity in embodiments 14–21.
Figure 15:
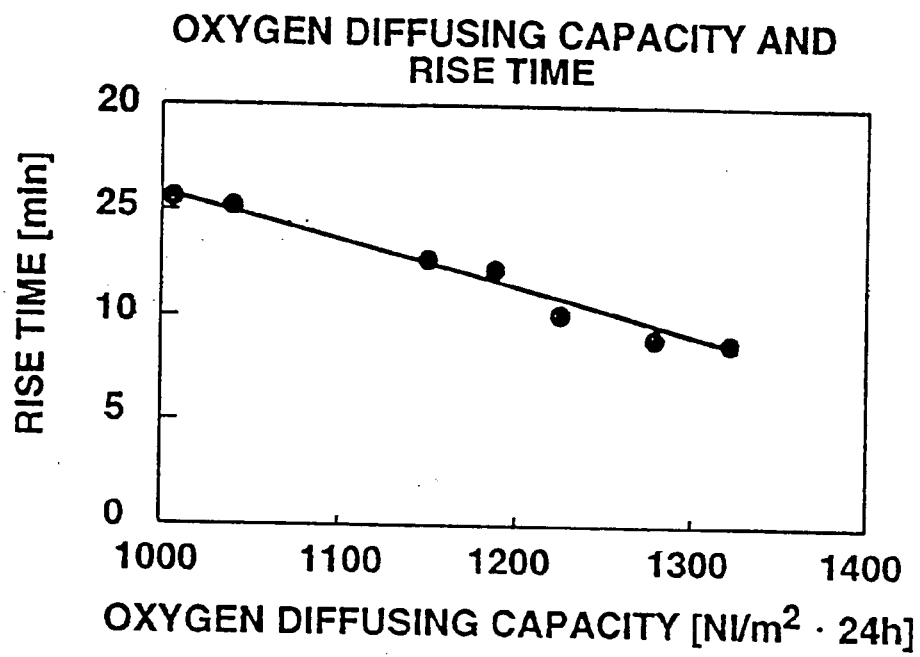
FIG. 15 is a diagram showing the properties of the relationship between the continuation time and the oxygen diffusing capacity in embodiments 14–21.

The results are shown in Table 3. FIG. 13 shows the relationship between oxygen diffusing capacity and maximum temperature. FIG. 14 shows the relationship between oxygen diffusing capacity and rise time. FIG. 15 shows the relationship between oxygen diffusing capacity and continuation time. The squares ($R^2$: contribution ratio) of the correlation coefficient, between the oxygen diffusing capacity and the rise time, maximum temperature, and continuation time, at the point where each approaches linearity, were 0.968 for the maximum temperature, 0.887 for the rise time, and 0.961 for the continuation time. In this way, strong correlations of these with oxygen diffusing capacity were confirmed.

TABLE 3

| Example | Oxygen diffusing capacity (Nl/m² 24 h) | Maximum temperature (° C.) | Rise time (min) | Continuation time (h) |
| --- | --- | --- | --- | --- |
| 14 | 1042 | 54.7 | 10.3 | 15.2 |
| 15 | 1148 | 58.4 | 9.0 | 12.5 |
| 16 | 1005 | 53.2 | 10.5 | 15.2 |
| 17 | 1185 | 58.9 | 8.9 | 12.2 |
| 18 | 1222 | 31.9 | 8.0 | 9.9 |
| 19 | 1319 | 63.0 | 7.9 | 8.6 |
| 20 | 1273 | 63.4 | 7.0 | 8.9 |
| 21 | 1315 | 63.7 | 7.7 | 9.0 |

Examples 22–28

Examples 22–28 are examples of shoe heating packets relating to the present invention.

Seven types of gas permeable packing material were prepared; these had oxygen diffusing capacities of 4800–6300 Nl/m² 24h and comprised nylon nonwoven fabric with a basis weight of 50 g/m² laminated to 100 μm thick polyethylene porous film with pores having a maximum diameter of 1.1 μm. These seven types of gas permeable packing materials were placed in contact with sheets of nylon nonwoven fabric with a basis weight of 50 g/m² laminated to 50 μm thick polyethylene film, in such a manner that the polyethylene surfaces of each were in contact. These were cut in the shape of a horse's hoof, 8.8 cm long and 6.6 cm wide. The edges were heat sealed to form pouches. These pouches were filled with 14 g of a heat generating composition comprising 66.4 wt % iron powder, 6.4 wt % activated carbon, 1.5 wt % sodium chloride, 22.2 wt % water, 3.1 wt % pearlite powder, and 0.4 wt % highly hydrophilic resin; inner pouches were prepared.

These inner pouches were then sealed within non-gas permeable outer pouches to form shoe heating packets. These were let stand for one week at 25° C.

These inner pouches were removed from the outer pouches. The shoe heating packets, having two sheets of gauze above and below, were placed on an aluminum panel and 4 mm thick rubber panel, layered in that order on a styrene foam, at a temperature of 20° C. The shoe heating packets were packed with three sheets of rubber and then two sheets of flannel. The heating characteristics were then measured. Table 4 shows the results.

The squares ($R^2$: contribution ratio) of the correlation coefficient, between the oxygen diffusing capacity and the rise time, maximum temperature, and continuation time, at the point where each approaches linearity, were 0.930 for the maximum temperature, 0.966 for the rise time, and 0.982 for the continuation time. In this way, strong correlations of these with oxygen diffusing capacity were confirmed. Moreover, the inner pouches of the shoe heating packets in example 23 and example 24 were inserted in work shoes with the gas permeable surface upwards; adult males engaged in light work in an environment with a 5° C. outside temperature. As a result, it was found that these both maintained comfortable temperatures.

TABLE 4

| Example | Oxygen diffusing capacity (Nl/m² 24 h) | Maximum temperature (° C.) | Rise time (min) | Continuation time (h) |
|---|---|---|---|---|
| 22 | 4800 | 40.5 | 14.0 | 7.5 |
| 23 | 5600 | 41.5 | 10.5 | 6.2 |
| 24 | 6000 | 42.5 | 8.6 | 5.4 |
| 25 | 5800 | 42.0 | 9.6 | 6.0 |
| 26 | 5950 | 42.5 | 9.0 | 5.6 |
| 27 | 5830 | 42.0 | 9.0 | 6.0 |
| 28 | 6300 | 43.5 | 6.0 | 5.0 | comparison examples 1–8

Figure 16:
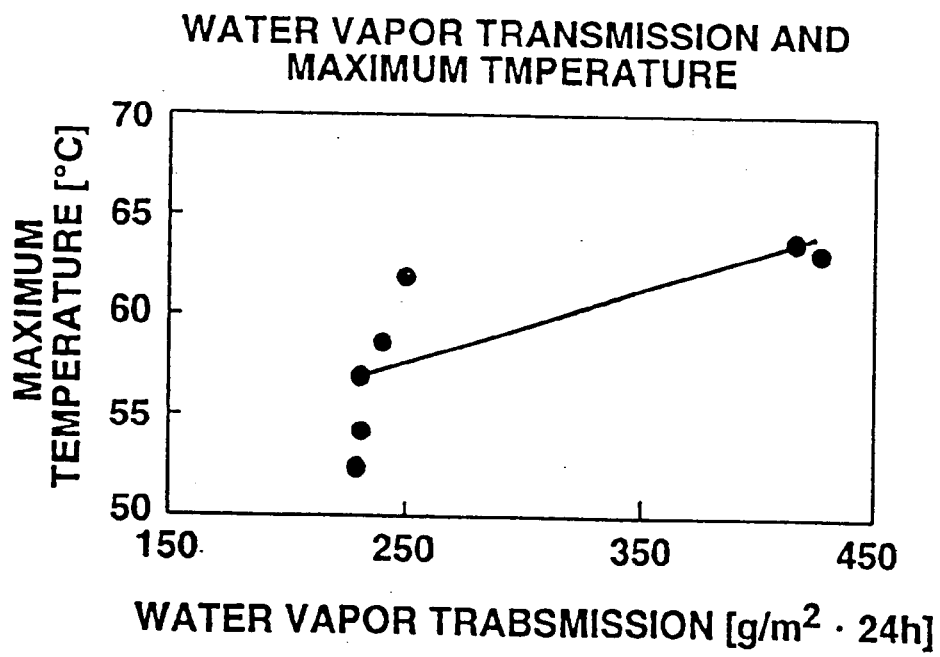
FIG. 16 is a diagram showing the properties of the relationship between the maximum temperature and water vapor permeability in embodiments 14–21.

The water vapor transmission of the same eight types of gas permeable packing material used in examples 14–21 was measured using the method stipulated in JIS Z 0208. Table 5 shows the results. Since these gas permeable packing materials were the same as the packing materials in examples 14–21, water vapor transmission could be correlated with the heating test results for examples 14–21. FIG. 16 shows the relationship between water vapor transmission and maximum temperature. The data in FIG. 16 confirm that maximum temperature changes greatly, even though the difference in water vapor transmission is low in the section containing the low values for water vapor transmission. Also, the squares ($R^2$: contribution ratio) of the correlation coefficient, between water vapor transmission and the rise time, maximum temperature, and continuation time, at the point where each approaches linearity, were 0.641 for the maximum temperature, 0.617 for the rise time, and 0.684 for the continuation time. In this way, it was found that the correlation between heating characteristics and water vapor transmission was very weak.

TABLE 5

| Comparison example | Water vapor transmission g/m² day |
|---|---|
| 1 | 230.8 |
| 2 | 241.3 |
| 3 | 227.7 |
| 4 | 238.2 |
| 5 | 250.5 |
| 6 | 428.6 |
| 7 | 417.9 |
| 8 | 417.0 |

Comparison example 9

The gas permeable packing material was prepared by forming 31 rows within a width of 32 mm of slit-shaped holes, at intervals of 4 mm, in a non-gas permeable packing material of nylon nonwoven fabric (Asahi Chemical Industry, N5051) laminated to 50 micron thick polyethylene film, using a hole making device with a rotary blade having pin-like protrusions. The pores formed in this manner had equivalent diameters of 0.1–0.15 mm. The gas permeability of this gas permeable packing material was 7 sec/100 ml, as measured with the Gurley gas permeability tester stipulated in JIS P 8117. This gas permeable packing material was used as one surface and a non-gas permeable packing material, comprising polyethylene, adhesive, and releasing paper laminated together in that order, was used as the other surface. A 96 mm×70 mm pouch was formed by placing these materials together with the polyethylene surfaces in contact and then heat sealing three sides. The pouch was filled with 13 g of a heat generating composition comprising 53 wt % iron powder, 8 wt % activated carbon, 7 wt % sawdust, 4 wt % table salt, and 28 wt % water. The pouch was heat sealed to form flat inner pouches. This was then sealed within a non-gas permeable outer pouch.

The heating characteristics of the heating pouch were measured in the same way as example 1–9. Table 6 shows the results.

Comparison Example 10

The gas permeability of the same gas permeable packing material used in example 11 was 12000 sec/100 ml as measured using the Gurley gas permeability measuring instrument stipulated in JIS P 8117. This gas permeable packing material was used as one surface and a non-gas permeable packing material, comprising polyethylene, adhesive, and releasing paper laminated together in that order, was used as the other surface. A 96 mm×70 mm pouch was formed by placing these materials together with the polyethylene surfaces in contact and then heat sealing three sides. The pouch was filled with 13 g of a heat generating composition comprising 53 wt % iron powder, 8 wt % activated carbon, 7 wt % sawdust, 4 wt % table salt, and 28 wt % water. The pouch was heat sealed to form flat inner pouches. This was then sealed within a non-gas permeable outer pouch.

The heating characteristics of the heating pouch were measured in the same way as example 1–9. Table 6 shows the results. The heating capacities were similar, regardless of the great difference between comparison example 9 and the Gurley gas permeability.

TABLE 6

| Comparison example | Gurley gas permeability (sec/100 ml) | Maximum temperature (° C.) | Rise time (min) | Continuation time (h) |
|---|---|---|---|---|
| 9 | 7 | 59.1 | 6.6 | 10.5 |
| 10 | 12000 | 58.2 | 6.6 | 11.5 |

INDUSTRIAL APPLICABILITY

The method for measuring oxygen diffusing capacity and apparatus for measuring oxygen diffusing capacity relating to the present invention make it possible to measure the gas permeability of the gas permeable packing material quickly and with good precision; the measured value of oxygen diffusing capacity correlates strongly to heating characteristics. In other words, (1) the present invention can find oxygen diffusing capacity in a short period of time, regardless of pore diameter sizes. (2) Even for different types of gas permeable packing materials, the measured values of oxygen diffusing capacity correlate to heating characteristics and can be compared without further processing. (3) For these reasons, the design and quality control for heating packets becomes easy. And (4) it becomes possible to establish the desired heating characteristics with a high level of precision by stipulating with oxygen diffusing capacity the gas permeable packing material for body heating packets, pocket heating packets, or shoe heating packets.

The heating packets relating to the present invention (1) are heating packets having optimal heating characteristics for a variety of uses, such as body heating packets, pocket heating packets, or shoe heating packets. The heating packets relating to the present invention (2) have heating characteristics corresponding to the various uses as body heating packets, pocket heating packets, or shoe heating packets, even for varying pore diameters and types of gas permeable packing materials. The heating packets relating to the present invention (3) are shoe heating packets with superior and never before seen temperature characteristics.

What is claimed is:

1. A method for measuring oxygen diffusing capacity of gas permeable packing materials comprising the steps of:

exposing one surface of a gas permeable packing material to uncontrolled, fresh air from the atmosphere;

scavenging the opposite surface with a carrier gas which does not include oxygen; and measuring the gas permeability of the gas permeable packing material from the concentration of oxygen gas in said carrier gas after scavenging.

2. The method for measuring oxygen diffusing capacity according to claim 1, wherein said carrier gas is nitrogen gas.

3. The method for measuring oxygen diffusing capacity according to claim 1, wherein the total pressure difference of the atmospheric pressure and carrier gas pressure contacting the gas permeable packing material is 3 mmH$_2$O or less.

4. The method according to claims 1–3, wherein the flow rate of said carrier gas is 50–2000 ml/cm$^2$·h per unit measured area of the gas permeable packing material.

5. The method according to claim 4, wherein the flow rate of the carrier gas is 100–500 ml/cm$^2$·h.

6. A heating packet comprising:

a heat generating composition, which generates heat when in contact with the oxygen in air, stored within a gas permeable inner pouch and further sealed within a non-gas permeable outer pouch, wherein one surface of the inner pouch is a gas permeable packing material with an oxygen diffusing capacity measured according to the method of claim 1.

7. A heating packet according to claim 6, wherein said heating packet is a body heating packet, wherein said gas permeable packing material has an oxygen diffusing capacity corresponding to a range of 1100±220 Nl/m$^2$ 24 h measured when one surface of said gas permeable packing material is exposed to the atmosphere and the other surface is scavenged with a carrier gas, not including oxygen, at a flow rate of 0.193 Nl/cm$^2$ h per unit area of the gas permeable packing material.

8. A heating packet according to claim 6, wherein said heating packet is a pocket heating packet, wherein said gas permeable packing material has an oxygen diffusing capacity corresponding to a range of 1600±350 Nl/m$^2$ 24 h measured when one surface of said gas permeable packing material is exposed to the atmosphere and the other surface is scavenged with a carrier gas, not including oxygen, at a flow rate of 0.193 Nl/cm$^2$ h per unit area of the gas permeable packing material.

9. A heating packet according to claim 6, wherein said heating packet is a shoe heating packet, wherein said gas permeable packing material has an oxygen diffusing capacity corresponding to a range of 5500±1100 Nl/m$^2$ 24 h measured when one surface of said gas permeable packing material is exposed to the atmosphere and the other surface is scavenged with a carrier gas, not including oxygen, at a flow rate of 0.193 Nl/cm$^2$ h per unit area of the gas permeable packing material.

10. The heating packets according to claims 7–9, wherein said carrier gas is nitrogen gas.

11. An apparatus for measuring oxygen diffusing capacity of gas permeable packing materials comprising a diffuser wherein one surface of a gas permeable packing material is exposed to uncontrolled, fresh air from the atmosphere;

the opposite surface is scavenged with a carrier gas which does not include oxygen; and oxygen gas in the atmosphere diffuses through the gas permeable packing material to the side toward the carrier gas.

12. The apparatus for measuring oxygen diffusing capacity according to claim 11, wherein said carrier gas is nitrogen gas.

13. The apparatus for measuring oxygen diffusing capacity according to claim 11, wherein the diffuser comprises at least one carrier gas supply tube and at least one exhaust tube.

14. The apparatus for measuring oxygen diffusing capacity according to claim 11, comprising an oxygen concentration detector inside the chamber of the diffuser and/or via the exhaust tube of the diffuser.

15. The apparatus for measuring oxygen diffusing capacity according to claim 11, wherein an exhaust pump is connected to the exhaust tube.

16. The apparatus according to claims 11–15, wherein the flow rate of said carrier gas is 50–2000 ml/cm$^2$·h per unit measured area of the gas permeable packing material.

17. The apparatus according to claim 16, wherein the flow rate of the carrier gas is 100–500 ml/cm$^2$·h.

* * * * *